United States Patent [19]

Rollema et al.

[11] Patent Number: 5,331,548
[45] Date of Patent: Jul. 19, 1994

[54] METHOD AND SYSTEM FOR ON-LINE MEASUREMENT, STORAGE, RETRIEVAL AND ANALYSIS OF URODYNAMICAL DATA

[76] Inventors: Harm J. Rollema, St. Josefstraat, 6245 LN Oost - Maarland (Eijsden); Ron van Mastrigt, Vryland 4, Mijnsheerenland (Dorp) both of Netherlands

[21] Appl. No.: 783,045

[22] Filed: Oct. 28, 1991

[51] Int. Cl.$^5$ .............................................. A61B 10/00
[52] U.S. Cl. .................. 364/413.02; 128/774
[58] Field of Search ............ 364/413.02, 413.01; 128/748, 782, 774; 604/21, 118

[56] References Cited

U.S. PATENT DOCUMENTS

| | | | |
|---|---|---|---|
| 4,063,548 | 12/1977 | Klatt et al. | 128/2 R |
| 4,073,287 | 2/1978 | Bradley et al. | 128/2 R |
| 4,191,196 | 3/1980 | Bradley et al. | 128/733 |
| 4,217,911 | 8/1980 | Layton | 128/748 |
| 4,407,301 | 10/1983 | Streisinger | 128/774 |
| 4,538,621 | 9/1985 | Jarczyn | 128/748 |
| 4,612,939 | 9/1986 | Robertson | 128/774 |
| 4,825,875 | 5/1989 | Ninan et al. | 128/748 |
| 5,062,304 | 11/1991 | Van Buskirk et al. | 73/861 |
| 5,167,237 | 12/1992 | Rabin et al. | 128/748 |

*Primary Examiner*—Roy N. Envall, Jr.
*Assistant Examiner*—Andrew Bodendorf
*Attorney, Agent, or Firm*—David H. Judson

[57] ABSTRACT

A computerized urological diagnostic method and system for use, for example, in preoperative assessment of prostatectomy candidates and other therapeutical measures in patients (males and females) with voiding complaints. The system includes a digital processor, a database, suitable input/output devices, and pressure and flow rate trandsucers for measure the patient's isometric detrusor pressure immediately before voiding and detrusor pressure and flow rate during micturition. These signals are processed and displayed to provide the clinician with objective data of bladder contractility and urethral resistance. With such data, the clinician can make informed treatment decisions.

9 Claims, 4 Drawing Sheets

METHOD AND SYSTEM FOR ON-LINE MEASUREMENT, STORAGE, RETRIEVAL AND ANALYSIS OF URODYNAMICAL DATA

TECHNICAL FIELD

The present invention relates generally to computer-based methods and systems for enhancing clinical assessment and evaluation of urological disorders,

BACKGROUND OF THE INVENTION

Hundreds of thousands of operations are performed annually on benignly enlarged prostates. A significant percentage of all patients do not improve after the operation while others develop new difficulties such as incontinence and impotence. There is also a mortality rate associated with the operation.

Traditionally, the field of urology has not focused attention on differential diagnosis of "outflow obstruction" and "bladder failure" in order to assess candidates prostatectomy (which as used herein includes transurethral prostatic resection or "TURP"). It is one of the merits of this invention that such parameters, which have recently proven to be of value in the differential diagnosis, can now routinely be included in the assessment for prostatectomy.

Urodynamic measurement systems of the prior art traditionally include appropriate transducers for generating pressure and flow rate signals during voiding, i.e., micturition. From these signals, it is possible to generate and display a pressure/flow rate curve, i.e., a representation plotting the pressure in the bladder against the urinary flow rate during micturition. Some experienced urologists are able to analyze this data and differentiate between "seriously obstructed patients" and "certainly non-obstructed patients." Such assessment, however, is based on visual subjective inspection of the shape of the plot, without any quantitative specification. The treatment decision is thus based on this subjective impression of the treating urologist and other clinical observations and tests including rectal palpation, residual urine assessed by ultrasound of the bladder, ultrasound of the prostate, free uroflowmetry and optional cystoscopy. None of these examinations, however, supply an objective, quantitative measure to determine either the degree of obstruction or the degree of bladder failure.

Thus, in the prior art even experienced urologists cannot objectively assess the indication for therapeutic interventions or evaluate their effect. This is also true for gynecologists who at present have no objective means to make a differential diagnosis between women with voiding complaints due to "urinary outflow obstruction" and/or impaired detrusor contractility.

BRIEF SUMMARY OF THE INVENTION

It is an object of the present invention to provide a computer-controlled method and system for preoperative assessment of male prostatectomy or female bladder neck incision candidates.

It is a further object of the invention to provide computerized methods and systems for objective and selective quantification of bladder contractility and urethral resistance in men and women.

It is still another object to provide a computer-controlled method and system for accurate separation of patients with bladder outflow obstruction from those with detrusor contractility failure.

It is yet another specific object of the invention to provide a computer system that is easy-to-use and that interfaces directly with a urodynamical measurement system to provide on-line measurement and quantification of a patient's urethral resistance and detrusor contractility.

It is another object to provide computerized methods and systems for predicting the clinical result of contemplated surgical procedures (such as prostectomy, bladder neck incision and anti-incontinence surgery), non-surgical therapeutical procedures (such as pharmaceutical treatment, hyperthermia, balloon dilatation and prostatic stents), as well as for evaluating bladder decompensation before and after any such procedure.

It is still a further object to provide a system for objective quantitative assessment of the effectiveness of new therapeutical methods and techniques for treatment of micturition disorders.

A further object is to provide a simple and reliable computerized diagnostic method and system for use by urologists, gynecologists and their assistants to facilitate prompt and accurate assessment of urological disorders.

It is another object to provide a computer software system for on-line measurement, storage, retrieval and analysis of urodynamic data for preoperative and postoperative assessment of both male and female urological disorders.

The foregoing has outlined some of the more pertinent objects of the present invention. These objects should, be construed to be merely illustrative of some of the more prominent features and applications of the invention. Many other beneficial results can be attained by applying the disclosed invention in a different manner of modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference should be made to the following Detailed Description taken in connection with the accompanying drawings in which.

DETAILED DESCRIPTION

Figure 1:
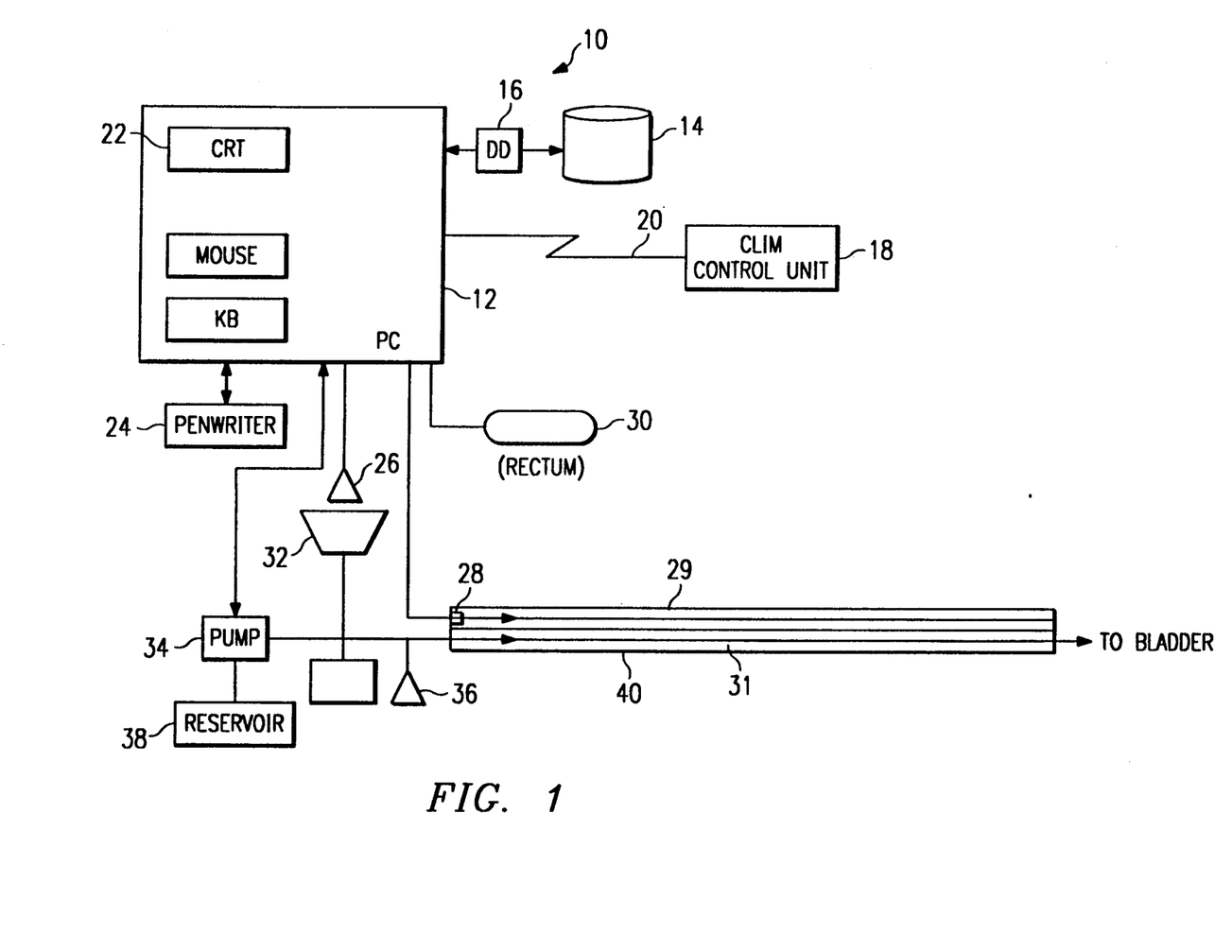
FIG. 1 is a simplified block diagram of a computerized system for assessing urological disorders according to the present invention.

Referring now to FIG. 1, a computer system 10 of tile present invention comprises a digital processor such as an IBM-compatible personal computer 12 with appropriate hard disk storage 14 and associated disk drive 16. A control unit 18 for the system 10 is connected to the personal computer 12 preferably, but not necessarily, via an infrared or wireless transmission link 20. The personal computer 12 has a conventional video display terminal 22 and the system also preferably includes a 4–6 channel penwriter 24. The various input signals are provided to the system 10 via a flow transducer 26 and a pair of (microtip) pressure transducers 28 and 30 for measuring intravesical and intrarectal pressure. The system includes appropriate amplifying and other signal processing circuitry. To enhance response time, the flow transducer 26 preferably measures flow rate directly as opposed to deriving the value from volume measurements. One suitable product is the rotating disk transducer, Dantec Model No. Urodyn 1000. The flow rate transducer 26 is supported in a suitable micturition stand 32. A (peristaltic) pump 34 and filling volume sensor 36 are supported on the stand 32. A reservoir 38 filled with a test fluid, e.g., saline, is connected to the pump 34.

On-line measurement of urodynamic data is facilitated in the clinical environment through the use of one or more catheters. In particular, if a transurethral route is taken, titan a pair of catheters is required. One catheter is used as a filling catheter to fill the bladder while the other catheter supports the pressure transducer 28. (Actually, the pressure transducer 28 is supported on the outer end of the catheter and the catheter is made air-tight such that an indirect pressure measurement is effected). The filling catheter, inserted via the transurethral route, is connected to the reservoir 38 through the pump 34. In particular, the patient to be tested is given a local anesthetic, and the catheter is inserted via the urethra into the bladder. The second (microtip) pressure measuring catheter is also inserted via the urethra into the bladder. Prior to micturation, the filling catheter is removed.

Alternatively, it is possible to use a suprapubic route as opposed to the transurethral route, in which case only one catheter is required. The bladder is filled via the suprapubical transcutaneous route by puncturing the bladder with the aid of a cystocath, ±2.0 c.m. above or below the pubic bone, after injection of a local anesthetic into the skin at the puncture location. As seen in FIG. 1, the catheter is preferably a 9 Fr-PVC suprapubic double lumen catheter having a first channel 29 and a second channel 31. The first channel 29 is connected to the saline pump 34 and the second channel 31 is used to support one of the microtip pressure transducers 28. As will be described, the invention uses for analysis the subtracted detrusor pressure (intravesical pressure minus intrarectal pressure). The other pressure transducer 30 is supported in the patient's rectum and used as a measure of intraabdominal pressure, which acts as a reference to the intravesical pressure measured by the pressure transducer 28.

The preferred testing protocol is as follows. Three times in succession the patient's bladder is filled with saline, at medium filling rate (e.g., 40 ml/min), via the first channel of the catheter. One test may be sufficient as well (i.e., one filling/voiding cycle). When the patient experiences an urge to void, he/she voids into the flow transducer 26. Via a switch box that is part of the control unit 18, the control program (as will be described) is triggered to begin and then cease storage of relevant signals. These signals include pressure and flow rate during micturation or bladder contraction, as well as the isometric detrusor pressure just before flow started. If the signals are in analog form, they are converted to digital form (by a suitable analog-to-digital converter) and stored in the database 14. The penwriter 24 outputs some or all of the monitored signals including intravesical pressure transducer 28), intraabdominal pressure (from transducer 30), subtracted detrusor pressure (the output of transducer 28 minus the output of transducer 30), flow rate (from transducer 26), etc. By recording such signals on the penwriter 24, the video display 22 is left free for displaying other more pertinent data as well be described. After voiding, residual urine is also measured directly by emptying the bladder via the double lumen catheter or via the transurethral filling catheter.

According to a feature of the invention, the computer processing system includes a software control program supported on the personal computer 12, for retrieving, displaying and analyzing such urodynamic data to assist the clinician in characterizing the patient's true physical condition. In part, the software control program facilitates accurate separation of patients with bladder outflow obstruction from those with detrusor contractility failure. Differential diagnosis of such conditions enable the clinician to more accurately predict the clinical result of contemplated surgical procedures, such as prostatectomy, and of non-surgical procedures. The program also enables objective quantitative assessment of the effectiveness of new therapeutical methods and techniques for treatment of micturition disorders.

Figure 2A:
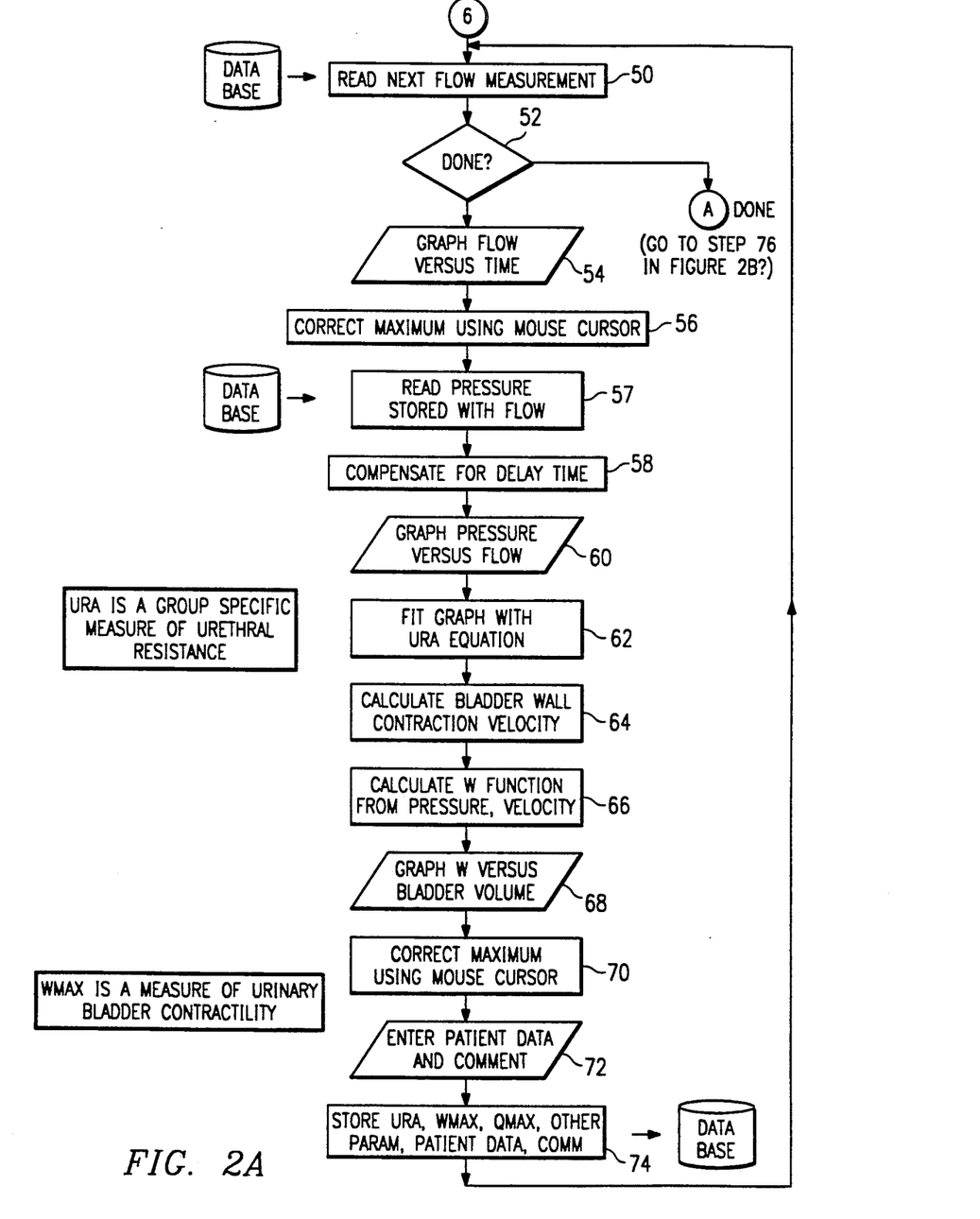
FIG. 2A is a flowchart representation of a flow rate analysis routine used in the processing system of FIG. 1.

Referring now to FIG. 2A, the analysis routine begins after an appropriate number (e.g., three (3) but minimally one) of bladder filling/voiding tests are run and the resultant urodynamic signals are digitized and stored in the database. At step 50, the routine retrieves from the database 14 a flow rate measurement from one of the preferably three (3) tests. A test is done at step 52 to determine if the flow rate measurement has been previously evaluated. If not, tile routine then continues at step 54 to generate a plot of flow rate versus time. This plot is displayed on the video terminal 22 at step 54. The routine then identifies and displays on the screen a flow rate value considered to be a maximum, and identified as a variable $Q_{max}$. The clinician can then correct the proposed value using a cursor of the personal computer 12. This correction is effected at step 56 and serves to eliminate artifacts, which may occur due to measured errors, e.g., interference with the flow transducer 26. The routine then continues at step 57 to retrieve the pressure data corresponding to the flow rate measurement being analyzed. At step 58, the routine compensates for the time delay that occurs between the pressure and flow rate measurements. Such delay occurs because the flow transducer is separated from the pressure transducer by approximately 0.5 meter in the urodynamic setup and the flow rate measured at a certain moment is related to the detrusor pressure measured earlier in time. To compensate for this lag time, the detrusor pressure is right-shifted a predetermined amount, i.e., equal to approximately 0.5–0.8 seconds, on the display.

OBSTRUCTION PARAMETER URA

Figure 3:
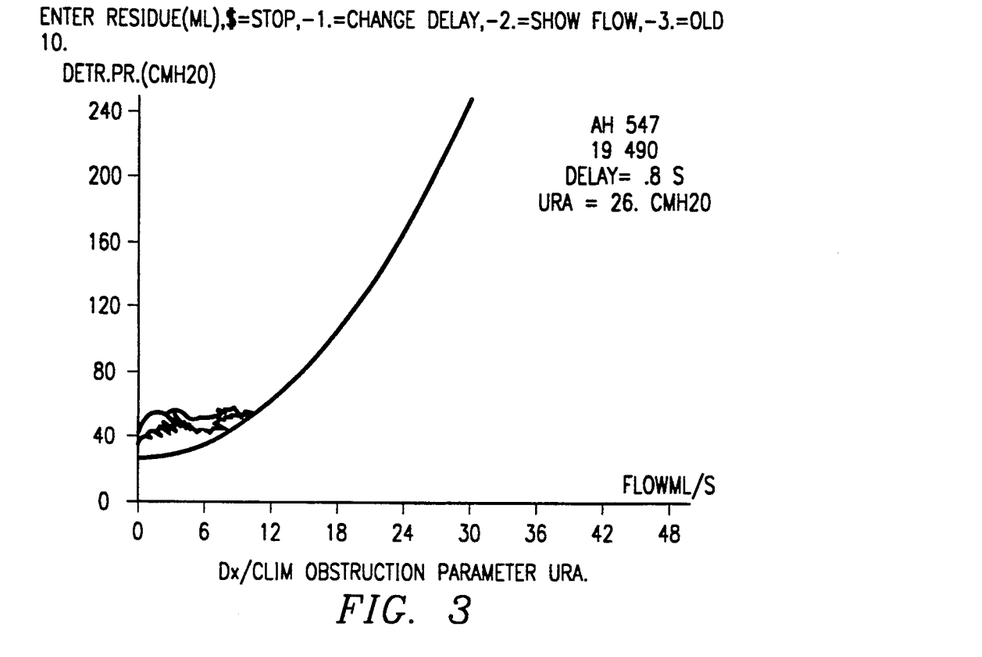
FIG. 3 is a representative plot of pressure as a function of flow rate generated by the control program of the present invention.

At step 60, a plot or pressure versus flow rate is generated and displayed on the video display 22. One such plot is shown, for example, in FIG. 3. The routine continues at step 62 by fitting the pressure/flow rate plot generated in step 60 with a predetermined quadratic urethral resistance relation set forth below. The quadratic resistance relation is characterized by two (2) parameters: its intercept on the pressure (i.e, the "y") axis, and its curvature. Experimentally, it has been established that a group-specific relation exists between these two parameters, i.e., that steeper curves generally also intercept the pressure axis at a higher value. This means that within a group of patients (e.g., adults), the urethal resistance can be characterized with one parameter only. This one parameter can be calculated from one representative point in the pressure flow data, e.g., the point of maximum flow. Arbitrarily, the intercept on the pressure axis was chosen as the one representative parameter.

In particular, at step 62 the routine determines the intersection of the quadratic resistance relation with the pressure axis of the pressure/flow rate plot. This intersection, arbitrarily selected as the representative parameter (as described above), is then defined as the urethral resistance parameter "URA." URA is a group specific measure (valid for a specific group of patients, males, females, etc.) of urethral resistance.

Contraction Strength Variable W

Of the various methods of assessing the strength of a detrusor contraction during voiding, the most attractive is the calculation of the external mechanical power generated (detrusor pressure×flow rate). However, this value is dependent on the volume in the bladder and is not constant for a constant contraction strength. It falls to zero if the contraction is isovolumetric (i.e., if detrusor pressure=0). Therefore a modified form has been adopted in which these objections are overcome.

Specifically, the contraction of the detrusor is governed by the so-called Hill equation, which describes the relation between the tension developed and the velocity of shortening of the contracting muscle. The equation may be written in terms of the pressure $P_{det}$ developed by the complete bladder (which is assumed to be spherical) and the velocity of shortening of the detrusor circumference $V_{det}$ as:

$$(P_{det}+a)(V_{det}+b)5\ ab \tag{A1}$$

Where "a" and "b" are experimentally-derived contractility constants. The approximate median values for a and b are 25 cm ($H_2O$) and 6 ram/s, respectively. The above form of the equation is convenient because its two adjustable parameters, the isovolumetric detrusor pressure and the physiological maximum value of the detrusor shortening velocity, are normally roughly independent of the volume in the bladder. Thus the left-hand side of equation A1 is approximately constant for fixed contraction strength, irrespective of the volume in the bladder, and it also increases with increase of $P_{det}$ and/or $V_{det}$. It is therefore a possible volume-independent measure of contraction strength. To ensure a value of zero when there is no contraction at all, it is appropriate to subtract ab from the left-hand side of equation A1. Because $P_{det} \times V_{det}$ is approximately equal to 2 times the external mechanical power developed by the detrusor divided by the surface area of the bladder, it is appropriate to divide the resulting function by $2\pi$. The resulting measure of detrusor contraction strength is thus:

$$WF=[(O_{det}+a)(v_{det}+b)-ab]/2\pi \tag{A2}$$

WF may be considered approximately as the mechanical power per unit area of bladder surface developed by the contracting detrusor, modified to allow for the finite power necessary to sustain an isovolumetric contraction or to shorten at high velocity under zero load.

The detrusor shortening velocity variable $v_{det}$ is calculated from the equation:

$$v_{det}=Q/2[3(V+V_t)/4\pi]^{\frac{2}{3}} \tag{A3}$$

in which the bladder is treated as a thick-walled sphere having a lumen of volume V. Q is the measured volume flow rate of urine, and $V_t$ represents the volume of noncontracting tissue enclosed by the effectively contracting detrusor tissue near the end of bladder emptying. If the bladder is not spherical, then $v_{det}$ represents an average velocity of shortening of the detrusor circumference. V is calculated by integrating Q backward from the end of voiding, allowing for any residual urine. In principle, the value of $P_{det}$ used in equation A1 should be delayed by 0.5–0.8 s in order to allow for the time delay in measuring Q.

To calculate WF, approximate median values for a and b (25 cm $H_2O$ and 6 mm/s), respectively, are used. Experimental tests showed that the value of WF was not very sensitive to changes in these assumed values. Estimates of $V_t$ have ranged from 2 to 50 ml. Changes in this value affect WF significantly one at the end of voidings with little residual urine. If too small a value of $V_t$ is assumed, WF may fluctuate significantly under these circumstances. The anatomically reasonable value of 10 ml eliminates such artifacts and is used in the calculations.

WF can be used to measure detrusor contraction strength during both voiding and filling. During filling WF is directly proportional to $P_{det}$ (see equation A2). With tile assumed value of b WF (in $W/m^2$ or $pW/mm^2$) is approximately equal to 0.1 $P_{det}$ (in cm $H_2O$).

Further Considerations Concerning the Above Models

The more-detailed models describing muscle contraction on the basis of cross-bridge interaction between actin and myosin filaments developed below can be shown to yield a force-velocity relation which is mathematically differently formulated, but approximates a hyperbola very closely. Such a hyperbolic force-velocity relation is characterized by three parameters: $F_o$, the intercept with the force axis, or the maximum isometric force the muscle can bare; $v_{max}$, the intercept with the velocity axis, or the maximum (unloaded) contraction velocity; and $aF_o^{-1}$, the degree of curvature of the hyperbola.

For the urinary bladder muscle and many other types of muscle $aF_o^{31\ 1}$ is generally found to be a constant of approximately 0.25 so that two parameters, $F_o$ and $v_{max}$, completely characterize the relation between force and shortening velocity of this muscle. Both variables depend severely on the length of the muscle. $F_o$ depends on muscle length, showing a clear optimum "working length" of the muscle, and $v_{max}$ shows a similar length dependence. striated muscle these length dependencies are explained by varying degrees of overlap of the actin and myosin filaments, which directly influence the number of cross-bridges that can be formed.

For smooth muscle a similar mechanism has been proposed, but since a regular filament arrangement is lacking in this type of muscle, there is no basis for such a mechanism. Indeed a length-dependent activation of smooth muscle has been proposed to account for the observed length dependencies. Apart from their dependence on length, $F_o$ and $v_{max}$ also depend on the degree of activation of the muscle. In an inactive muscle, both $F_o$ and $v_{max}$ are zero, and during the onset of stimulation both parameters somehow increase to a maximum that is maintained for some time depending on stimulus conditions. It is this maximum that is representative for the (myogenic) contractile properties of the muscle.

Power itself is not a useful variable to represent contraction strength as it is zero for zero pressure or zero flow rate. As a consequence, the power in a very high isometric contraction is zero, as is the power in a voiding with high flow rate at (almost) zero pressure, which is often seen in normal females. A proposed variable, W, overcomes this problem as it contains additive terms based on Hill's equation that make it non-zero if either flow rate or detrusor pressure is non-zero. In the normal case W slowly rises on bladder emptying as a result of the length dependence of $F_o$ and $v_{max}$. In case of failing voiding, W decreases prematurely, leaving residual urine.

The maximum of W during bladder emptying can be taken as a parameter of contractility; $W_{max}$ equals the product of $F_o$ with $W_{max}$ and a constant. The method of the present invention takes advantage of the above-identified models. Referring now back to FIG. 2A, at step 64, the routine calculates bladder wall contraction velocity and at step 66, the routine calculates a detrusor contractility strength function from the bladder wall contraction velocity calculated in step 64 and from the pressure data retrieved at step 57.

Figure 4:
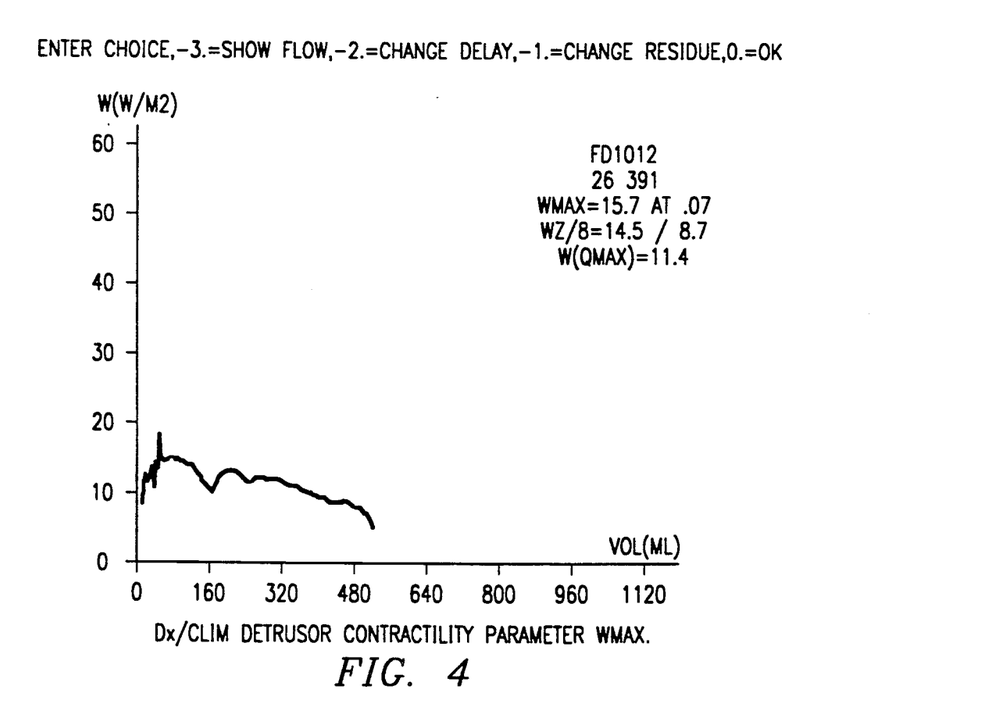
FIG. 4 is a representative plot of detrusor contractility as a function of bladder volume during micturition generated by the control program of the invention.

The routine then continues to step 68 to plot the contractility strength function versus bladder volume, as shown in representative FIG. 4. This plot represents detrusor contractility throughout micturition. The routine again indicates a proposed maximum value $W_{max}$ which the user can then correct (by inspecting the plot) at step 70 using the cursor. The patient data is then entered at step 72, and this data and the following urodynamic parameters are stored at step 74:

Qmax: maximum flowrate
Wmax: detrusor contractility parameter
URA: obstruction parameter
rV (Wmax): the relative volume at which Wmax occurred
W (Qmax): the value of W at the moment of maximum flowrate
W20: the value of W at a relative volume rV=0.20
W80: the value of W at a relative volume of rV=0.80
$T_{det}$ (max): the maximum detrusor pressure
Residual urine: the amount of urine that is left in the bladder after micturition The routine then returns to step 50 to retrieve the next detrusor pressure and flow rate measurement, i.e. from the next test.

Figure 2B:
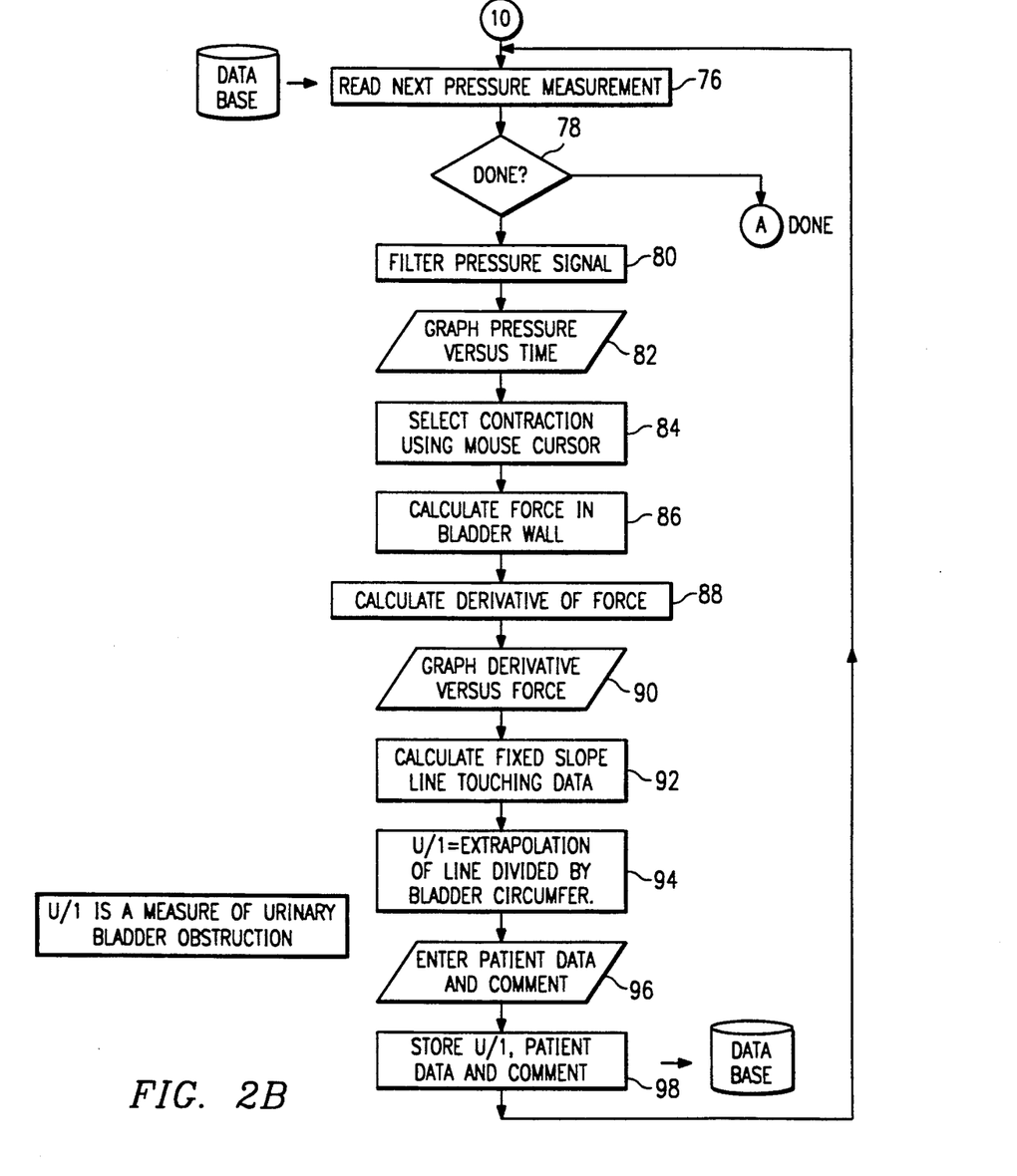
FIG. 2 is a flowchart representation of a pressure analysis routine used in the processing system of FIG. 1.

After the flow rate measurements for the three tests have been processed in this manner, the user may continue as shown in FIG. 2B. In particular, at step 76, the routine reads the oldest unprocessed contraction measurement from tile database. The routine filters the signal at step 80 with a moving low pass digital filter. The purpose of this filtering is to remove artifacts, e.g. electrical spikes, without losing essential information. A plot of pressure versus time is then generated and displayed at step 82.

Obstruction Parameter U/1 and Bladder Force

At step 84, the beginning and the end of the contraction are selected using the cursor. In particular, the screen shows the preceding part of the pressure signal before the contraction starts, the rise of the contraction and stops at the moment the flow rate starts. By moving the mouse cursor the operator indicates the beginning of the rising part and the end of the contraction, in fact the end of the signal (the point where flow rate starts).

Using this selected isometric portion of the contraction, the routine continues at step 86 and calculates the bladder wall force as a function. The derivative of the bladder wall force is then calculated at step 88. The routine then plots the derivative versus force at step 90.

If the series elasticity of smooth muscle formed a constant, i.e. obeyed one unchanging relation between its length and force, it would be possible to calculate properties of the contractile element from the time course of the development of isometric force of pressure in the urinary bladder. Unfortunately, as described above this is not the case. Alternatively, it has been shown by phase plot analysis that isometric force development in vitro is related to activation of tim contractile element rather than its shortening. In phase plots made from clinically measured isometric contractions, i.e. the detrusor pressure rise before the onset of micturition, a straight line part is much more difficult to recognize than in phase plots from isometric contractions measured in vitro. By fitting a straight line with preset slope to such "clinical" phase plots, a parameter (U) was obtained that was normalized by dividing it by the bladder circumference. The normalized parameter U/1 was extensively evaluated.

From this evaluation, it was concluded that the parameter U/1 derived from phase plots of the isometric detrusor pressure rise before the outset of micturition is biased by the urethral opening pressure to such a degree that it can be used as a measure for the degree of obstruction. Here it has been concluded that under clinical circumstances the information in the isometric development of pressure in the urinary bladder before the outset of micturition is very useful, but not necessarily with respect to measuring contractility.

Referring back to FIG. 2B, at step 92, the routine calculates a fixed slope line touching the derivative versus force curve. The parameter "U/1" is then calculated at step 94 by extrapolating the fixed slope line divided by a bladder circumference value. Experimental observation has shown this parameter to be linearly dependent on 1 (as described above). Therefore the parameter U is normalized by dividing it by 1. The U/1 parameter is a measure of urinary bladder outflow obstruction. Patient data is then entered at step 96, and the U/1 parameter and such patient data are stored at step 98.

The routine then recycles to obtain kite next pressure measurement.

The URA, U/1 and $W_{max}$ parameters have been found possess significant clinical predictive capability. A value of URA larger than a predetermined amount indicates "obstruction" ("OBS"). A value less than this amount indicates a non-obstructed ("NOBS") condition. Thus, based on the OBS or NOBS conclusion, the clinician can differentially diagnose or separate patients with bladder outflow obstruction from those with detrusor contractility failure. Based on clinical evaluations, the urethral resistance parameter URA has a sensitivity of approximately 90% and a specificity of 97% for this purpose. The U/1 parameter, while technically a measure of bladder contractility, also possesses a significant predictive capability for diagnosing an OBS condition because it effectively reflects the isometric detrusor pressure needed to overcome an obstruction, and more initial pressure will be required if such a condition exists. A value of $U/1 > 54$ $W/m^2$ indicates the presence of obstruction, while a value less than this amount makes the existence of an obstruction unlikely.

If both parameters (URA and U/1) are considered a straight line according to the equation:

$$U/1 + 2.58 * URA = 128,$$

then such time as plotted separates the OBS from the NOBS patients. If both obstruction parameters URA and U/1 are considered clinical data have shown that the confirmation has a sensitivity and specificity both of almost 100%.

A value of $W_{max}$ less than a predetermined amount (12.85 W/m$^2$) indicates detrusor contractility lower than normal. The $W_{max}$ parameter also accurately predicts the likelihood of residual postoperative urine in patients with low detrusor contractility; specifically, if $W_{max}$ is preoperatively less than the above-mentioned cutoff value, there is a high likelihood of residual urine post-operatively. The parameter $W_{max}$ characterizes urinary bladder contractility.

It should be appreciated by those skilled in the art that the specific embodiments disclosed above may be readily utilized as a basis for modifying or designing other structures for carrying out the same purposes of the present invention. For example, it is envisioned that other measures of urethral resistance and detrusor contractility be used in conjunction with the computerized system of the present invention. It should also be realized by those skilled in the art that such equivalent constructions do not depart from the spirit and scope of the invention as set forth in the appended claims.

What is claimed is:

1. A method, using a computer processing system, for preoperative assessment of a patient having prostatism symptoms or other symptoms associated with voiding disorders upon clinical evaluation, comprising the steps of:
    (a) measuring the patient's isometric detrusor pressure immediately before voiding and detrusor pressure and flow rate during voiding using pressure and flow rate transducers of a computer processing system, the computer processing system further including a digital processor, storage means, input means, and output means;
    (b) inputting and storing, to said computer processing system, the patient's isometric detrusor pressure immediately before voiding and detrusor pressure and flow rate during voiding measured in (a) in the computer processing system;
    (c) using the computer processing system to generate a plot of pressure as a function of flow rate during voiding;
    (d) adapting a urethral resistance relation to the plot generated in step (c) and using the computer processing system to generate a urethra resistance parameter URA;
    (e) using the computer processing system to generate a plot of detrusor contractility as a function of the patient's bladder volume during voiding; and
    (f) using said processor to calculate a maximum extrapolated rate of rise of the patient's isometric detrusor pressure and generate a contractility parameter U/1.

2. A computerized urological diagnostic system, comprising:
    a digital processor for controlling the operation of the diagnostic system;
    storage means connected to the processor for storing data;
    pressure and flow rate transducer means for measuring a patient's isometric detrusor pressure immediately before voiding and detrusor pressure and flow rate during voiding;
    a display connected to the digital processor for selectively displaying data derived from pressure and flow rate signals measured by the pressure and flow rate transducer means; and
    program control means for controlling the digital processor to effect presentation, by the display, of the data, the program control means including:
    first means for generating a plot of detrusor pressure as a function of flow rate during voiding;
    second means for determining an intersection of a fitted quadratic curve to the plot generated by the first means and generating a urethra resistance parameter URA;
    third means for generating a plot of detrusor contractility as a function of the patient's bladder volume during voiding; and
    fourth means for calculating a maximum extrapolated rate of rise of the patient's isometric detrusor pressure and generating a contractility parameter U/1.

3. The diagnostic system as described in claim 2 further including input means connected to the digital processor for selectively modifying the displayed data.

4. The diagnostic system as described in claim 2 further including:
    a catheter having first and second channels, the first laving an end in which the pressure transducer means is supported;
    a reservoir of fluid; and
    pump means controlled by the digital processor for delivering the fluid through the second channel of the catheter and into the patient's bladder.

5. The diagnostic system as described in claim 2 further including a penwriter for recording at leash one of the pressure and flow rate signals.

6. The diagnostic system as described in claim 2 wherein the first means of the program control means includes:
    means for generating a plot of flow rate; .
    means for retrieving pressure data stored in the storage means; and
    means for compensating for a time delay between the flow rate and pressure data.

7. The diagnostic system as described in claim 2 wherein the third means of the program control means includes:
    means for calculating bladder wall contraction velocity;
    means for receiving the pressure data and the bladder wall contraction velocity and calculating the bladder contractility strength.

8. The diagnostic system as described in claim 2 wherein the fourth means of the program control means includes:
    means for retrieving pressure data from the storage means;
    means for filtering a pressure-time plot of the pressure data as a function of time;
    means for selecting the isometric part of the contraction in the pressure-time plot;
    means responsive to the selected contraction value for calculating a bladder wall force;

means for calculating a derivative of the bladder wall force;

means for generating a plot of the bladder wall force derivative as a function of the bladder wall force; and means for calculating a fixed slope line touching the plot of the bladder wall force derivative as a function of the bladder wall force.

9. A computerized urological/gynecological diagnostic system, comprising:

a digital processor for controlling the operation of the diagnostic system;

storage means connected to the processor for storing data;

pressure and flow rate transducer means for measuring a patient's isometric detrusor pressure immediately before voiding and detrusor pressure and flow rate during voiding;

a display connected to the digital processor for selectively displaying data derived from pressure and flow rate signals measured by the pressure and flow rate transducer means; and program control means for controlling the digital processor to effect presentation, by the display, of the data, the program control means including:

first means, responsive to signals generated by the flow rate transducer means, for quantifying the patient's urethral resistance; and second means, responsive to signals generated by the pressure transducer means, for quantifying the patient's detrusor contractility.

* * * * *